United States Patent
Nakabayashi et al.

(10) Patent No.: US 9,899,788 B2
(45) Date of Patent: Feb. 20, 2018

(54) SOLID-STATE LASER DEVICE AND PHOTOACOUSTIC MEASUREMENT DEVICE

(71) Applicant: FUJIFILM Corporation, Tokyo (JP)

(72) Inventors: Koki Nakabayashi, Ashigarakami-gun (JP); Takuji Tada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 219 days.

(21) Appl. No.: 15/062,578

(22) Filed: Mar. 7, 2016

(65) Prior Publication Data
US 2016/0190762 A1 Jun. 30, 2016

Related U.S. Application Data

(63) Continuation of application No. PCT/JP2014/068059, filed on Jul. 7, 2014.

(30) Foreign Application Priority Data

Sep. 18, 2013 (JP) .................................. 2013-193199
Jun. 26, 2014 (JP) .................................. 2014-131451

(51) Int. Cl.
*H01S 3/092* (2006.01)
*H01S 3/093* (2006.01)
(Continued)

(52) U.S. Cl.
CPC .......... *H01S 3/025* (2013.01); *G01N 21/1702* (2013.01); *H01S 3/042* (2013.01);
(Continued)

(58) Field of Classification Search
CPC .......... H01S 3/025; H01S 3/092; H01S 3/042; G01N 21/1702
(Continued)

(56) References Cited

U.S. PATENT DOCUMENTS 5,867,518 A * 2/1999 Filgas .................. H01S 3/07 372/69
5,867,519 A * 2/1999 Filgas .................. H01S 3/07 372/100
(Continued)

FOREIGN PATENT DOCUMENTS

JP 10-125991 A 5/1998
JP 10-125993 A 5/1998
(Continued)

OTHER PUBLICATIONS

Japanese Office Action, dated Aug. 29, 2017 for corresponding Japanese Application No. 2016-200874, with English translation.
(Continued)

*Primary Examiner* — J M Saint Surin
(74) *Attorney, Agent, or Firm* — Birch, Stewart, Kolasch & Birch, LLP

(57) ABSTRACT

Disclosed are a solid-state laser device having an advantage of achieving simplification of a configuration and reduction in size, and a photoacoustic measurement device. In a solid-state laser device which accommodates a solid-state laser medium and an excitation light source having a rod-shaped portion, the excitation light source is provided to be pulled out of a laser chamber. An optical element which bends light is provided at a position separated from the rod-shaped portion such that at least a part of the optical element and at least a part of the rod-shaped portion are at the same position in the longitudinal direction of the rod-shaped portion. One resonator mirror is disposed at a position where bent light is incident. Optical components between the optical element and the resonator mirror are provided at positions separated from a path along which the excitation light source is pulled out.

20 Claims, 16 Drawing Sheets

(51) Int. Cl.
*H01S 3/081* (2006.01)
*G01N 21/17* (2006.01)
*H01S 3/042* (2006.01)
*H01S 3/02* (2006.01)
*H01S 3/115* (2006.01)

(52) U.S. Cl.
CPC ............ *H01S 3/0815* (2013.01); *H01S 3/092* (2013.01); *H01S 3/0931* (2013.01); *G01N 2201/06113* (2013.01); *H01S 3/115* (2013.01)

(58) Field of Classification Search
USPC .............................................. 73/655; 372/41
See application file for complete search history.

(56) References Cited

U.S. PATENT DOCUMENTS

| | | | | |
|---|---|---|---|---|
| 7,430,231 | B2* | 9/2008 | Luo | H01S 3/025 372/10 |
| 8,576,885 | B2* | 11/2013 | van Leeuwen | H01S 5/423 372/34 |
| 9,478,941 | B2* | 10/2016 | Gronenborn | H01S 3/08068 |
| 2007/0201532 | A1 | 8/2007 | Zhang et al. | |

FOREIGN PATENT DOCUMENTS

| | | |
|---|---|---|
| JP | 2000-514605 A | 10/2000 |
| JP | 4749236 B2 | 8/2011 |
| JP | 2013-74180 A | 4/2013 |
| WO | WO 98/06156 A1 | 2/1998 |

OTHER PUBLICATIONS

International Preliminary Report on Patentability dated Mar. 22, 2016, issued in PCT/JP2014/068059 (Form PCT/IB/373).
Written Opinion of the International Searching Authority dated Sep. 22, 2014, issued in PCT/JP2014/068059 (Form PCT/ISA/237).
International Search Report for PCT/JP2014/068059 (PCT/ISA/210) dated Sep. 22, 2014.
Written Opinion of the International Searching Authority for PCT/JP2014/068059 (PCT/ISA/237) dated Sep. 22, 2014.

* cited by examiner

SOLID-STATE LASER DEVICE AND PHOTOACOUSTIC MEASUREMENT DEVICE

CROSS-REFERENCE TO RELATED APPLICATIONS

This application is a Continuation of PCT International Application No. PCT/JP2014/068059 filed on Jul. 7, 2014, which claims priority under 35 U.S.C § 119(a) to Japanese Patent Application No. 2013-193199 filed on Sep. 18, 2013 and Japanese Patent Application No. 2014-131451 filed on Jun. 26, 2014. Each of the above application(s) is hereby expressly incorporated by reference, in its entirety, into the present application.

BACKGROUND OF THE INVENTION

1. Field of the Invention

The present invention relates to a solid-state laser device, and in particular, to a solid-state laser device in which an excitation light source and a solid-state laser medium are accommodated inside a laser chamber.

The present invention also relates to a photoacoustic measurement device using such a solid-state laser device.

2. Description of the Related Art

Hitherto, as one image inspection method which can noninvasively inspect a state inside an object, such as a living body, an ultrasonography method has been known. In ultrasonography, an ultrasound probe which can transmit and receive an ultrasonic wave is used. For example, if an ultrasonic wave is transmitted from the ultrasound probe to the living body, the ultrasonic wave advances through the inside of the living body, and is reflected from a tissue interface. The reflected ultrasonic wave is received by the ultrasound probe, and a distance is calculated based on the time until the reflected ultrasonic wave returns to the ultrasound probe, whereby it is possible to image a status inside the living body.

Furthermore, photoacoustic imaging which images the inside of a living body using a photoacoustic effect is known. In photoacoustic imaging, in general, the inside of the living body is irradiated with pulsed light, such as a pulsed laser beam. Inside the living body, a living body tissue absorbs energy of pulsed light, and an ultrasonic wave (photoacoustic signal) is generated due to adiabatic expansion caused by energy. The photoacoustic signal is detected by an ultrasound probe or the like, and a photoacoustic image is constituted based on a detection signal, whereby it is possible to visualize the inside of the living body based on the photoacoustic signal.

In a measurement of a photoacoustic wave, in general, it is necessary to emit pulsed light with high intensity, and for example, a flash lamp excited solid-state laser device is widely used for a light source. This type of solid-state laser device has, for example, a solid-state laser medium which is formed in a rod shape, and a flash lamp which excites the solid-state laser medium. In many cases, the solid-state laser medium and the flash lamp are accommodated inside a laser chamber having an internal space. In general, the inner wall surface of the laser chamber is provided with a reflection surface or a diffusion surface to allow efficient irradiation of the solid-state laser medium with excitation light emitted from the flash lamp, and a refrigerant which cools the solid-state laser medium and the flash lamp is supplied into the internal space of the laser chamber.

The excitation light source, such as the flash lamp, is a consumable, and needs to be replaced regularly. Furthermore, there is a widespread demand for reduction in the size of the solid-state laser device, in addition to a case of being used for measuring the photoacoustic wave.

JP1998-125993A (JP-H10-125993A) and JP1998-125991A (JP-H10-125991A) disclose an example of a solid-state laser device in which replacement of an excitation light source or reduction in size of the device is considered.

That is, JP1998-125993A (JP-H10-125993A) discloses a solid-state laser device in which an excitation lamp having a straight rod shape and a solid-state laser medium formed in a rod shape are accommodated inside a laser chamber in a state of being close to each other in parallel to each other. JP1998-125993A (JP-H10-125993A) discloses that an optical path between one (rear mirror) of a pair of resonator mirrors and the solid-state laser medium is bent in a transverse direction by the mirror in order to prevent enlargement of the solid-state laser device in the longitudinal direction of the solid-state laser medium. Furthermore, JP1998-125993A (JP-H10-125993A) discloses that, for replacing the rod-shaped excitation lamp, the excitation lamp is pulled out of the laser chamber in the lamp longitudinal direction, and the mirror is rotated along with a holder thereof in order to secure a space for pulling out.

JP1998-125991A (JP-H10-125991A) discloses a solid-state laser device in which an excitation lamp and a solid-state laser medium formed in a rod shape are accommodated inside a laser chamber. JP1998-125991A (JP-H10-125991A) also discloses that an optical path between one (rear mirror) of a pair of resonator mirrors and the solid-state laser medium is bent in a transverse direction by the mirror in order to prevent enlargement of the solid-state laser device in the longitudinal direction of the solid-state laser medium.

SUMMARY OF THE INVENTION

In the solid-state laser device disclosed in JP1998-125993A (JP-H10-125993A), as described above, the mirror which bends the optical path is provided, whereby it is considered that it is possible to prevent enlargement of the device to some extent.

However, in the solid-state laser device disclosed in JP1998-125993A (JP-H10-125993A), since the mirror for bending the optical path is disposed at a significantly long distance from the end surface of the solid-state laser medium (from FIGS. 2 and 5, also at a long distance from the end surface of the excitation lamp), the distance between the end surface of the solid-state laser medium and the rear mirror is inevitably and extremely extended. In this way, if the resonator mirror is disposed at a large distance from the end surface of the solid-state laser medium, and the resonator length is large, the device is increased in size, and in a case where pulse oscillation is caused, it is difficult to sufficiently reduce the pulse width of the pulsed laser beam. The above problem is also found in the solid-state laser device disclosed in JP1998-125991A (JP-H10-125991A).

In the solid-state laser device disclosed in JP1998-125993A (JP-H10-125993A), in a case where the mirror is rotated along with the holder thereof in order to secure the space for pulling the excitation lamp out of the laser chamber, there is a problem in that the structure of the device is complicated.

The invention has been accomplished in consideration of the above-described situation, and an object of the invention is to provide a solid-state laser device in which an excitation light source, such as a lamp, and a solid-state laser medium are accommodated inside a laser chamber, having advantages of allowing the excitation light source being easily pulled out of the laser chamber with a simple configuration and achieving sufficient reduction in size.

Another object of the invention is to provide a solid-state laser device and a photoacoustic measurement device which can be formed in a small size using the above-described solid-state laser device.

A solid-state laser device according to the invention includes a laser chamber which has an internal space, a solid-state laser medium, at least a part of which is accommodated in the laser chamber, an excitation light source which has a rod-shaped portion extending linearly, a part of the rod-shaped portion being provided inside the laser chamber as a portion emitting excitation light exciting the solid-state laser medium, and both end portions being provided outside the laser chamber, and a pair of resonator mirrors which resonate light emitted from both end portions of the excited solid-state laser medium. The rod-shaped portion of the excitation light source is provided to be moved in a longitudinal direction of the rod-shaped portion and pulled out of the laser chamber, an optical element which bends light emitted from one end surface of the solid-state laser medium in a transverse direction is provided to face the one end surface of the solid-state laser medium, the optical element is provided at a position separated from the rod-shaped portion such that at least a part of the optical element and at least a part of the rod-shaped portion are at the same position in the longitudinal direction of the rod-shaped portion, one of the pair of resonator mirrors is disposed at a position where light bent by the optical element is incident, and optical components between the optical element and the one resonator mirror are provided at positions separated from a path along which the rod-shaped portion of the excitation light source is pulled out.

It is assumed that "the optical components between the optical element and the one resonator mirror" include other optical components in a case where other optical components are disposed between both of them. Furthermore, "at least a part of the optical element and at least a part of the rod-shaped portion are at the same position in the longitudinal direction of the rod-shaped portion" means that, when a surface perpendicular to the longitudinal direction is considered, a surface including at least a part of the optical element is present within the total length range of the rod-shaped portion.

It is preferable that the solid-state laser device according to the invention has a configuration for generating a pulsed laser beam.

The optical element may be disposed on an optical path between a resonator mirror as a rear mirror and the solid-state laser medium, or may be disposed on an optical path between a resonator mirror as an output mirror and the solid-state laser medium.

As the optical element, for example, a prism or a mirror can be applied, and a Brewster polarizer or the like can also be applied.

As the excitation light source, a flash lamp can be suitably used.

It is preferable that the rod-shaped portion of the excitation light source is held in through holes formed in two wall portions of the laser chamber separated from each other in the longitudinal direction of the rod-shaped portion.

In the solid-state laser device of the invention, it is preferable that the solid-state laser medium is formed in a rod shape, and the solid-state laser medium is disposed parallel to the rod-shaped portion of the excitation light source.

In the solid-state laser device of the invention it is preferable that a refrigerant is supplied into the internal space of the laser chamber.

In the solid-state laser device of the invention, it is preferable that a diffusion member which diffuses and reflects excitation light emitted from the excitation light source is formed on an inner wall surface of the laser chamber.

In the solid-state laser device of the invention, it is preferable that a cylinder member which encapsulates an optical path between the solid-state laser medium and the optical element is provided, and in this case, the cylinder member may encapsulate the optical element.

Alternatively, in the solid-state laser device of the invention, it is preferable that a plate-shaped member is disposed between an optical path between the solid-state laser medium and the optical element and the excitation light source.

Alternatively, in the solid-state laser device of the invention, it is preferable that a light guide member is disposed on an optical path between the solid-state laser medium and the optical element.

Alternatively, in the solid-state laser device of the invention, it is preferable that, in a case where the optical element is a prism, the solid-state laser medium and the prism are optically connected directly to each other.

A photoacoustic measurement device according to the invention includes the solid-state laser device of the invention, a photoacoustic wave detection part which detects a photoacoustic wave generated inside an object by irradiating the object with laser light emitted from the solid-state laser device, and a signal processing part which performs a signal process based on the detected photoacoustic wave.

In the solid-state laser device of the invention, as described above, the rod-shaped portion of the excitation light source is provided to be moved in the longitudinal direction of the rod-shaped portion and pulled out of the laser chamber, the optical element which bends light emitted from the one end surface of the solid-state laser medium in a transverse direction is provided to face the one end surface of the solid-state laser medium, the optical element is provided at a position separated from the rod-shaped portion such that at least a part of the optical element and at least a part of the rod-shaped portion are at the same position in the longitudinal direction of the rod-shaped portion, one of the pair of resonator mirrors is disposed at a position where light bent by the optical element is incident, and the optical components between the optical element and the one resonator mirror are provided at positions separated from a path along which the rod-shaped portion of the excitation light source is pulled out; therefore, if the rod-shaped portion of the excitation light source is moved in the longitudinal direction and pulled out of the laser chamber, the rod-shaped portion does not interfere with any optical component, and the excitation light source can be simply removed from the laser chamber.

In this way, for pulling the rod-shaped portion of the excitation light source out of the laser chamber, it is not necessary to secure the space for moving and pulling the optical element out; therefore, the solid-state laser device of the invention has a simpler configuration compared to a solid-state laser device which has a configuration for moving the optical element.

The optical element is disposed such that at least a part of the optical element and at least a part of the rod-shaped portion are at the same position in the longitudinal direction of the rod-shaped portion of the excitation light source; therefore, it is possible to sufficiently reduce the distance between the end surface of the solid-state laser medium and the optical element, and consequently, to reduce the distance between the end surface of the solid-state laser medium and the resonator mirror. With this, it is possible to achieve sufficient reduction in the size of the device, and to reduce the resonator length, whereby it is possible to sufficiently reduce the pulse width in a case of generating the pulsed laser beam.

The photoacoustic measurement device according to the invention can be formed in a sufficiently small size since the solid-state laser device according to the invention described above is provided as a light source.

DESCRIPTION OF THE PREFERRED EMBODIMENTS

Figure 1:
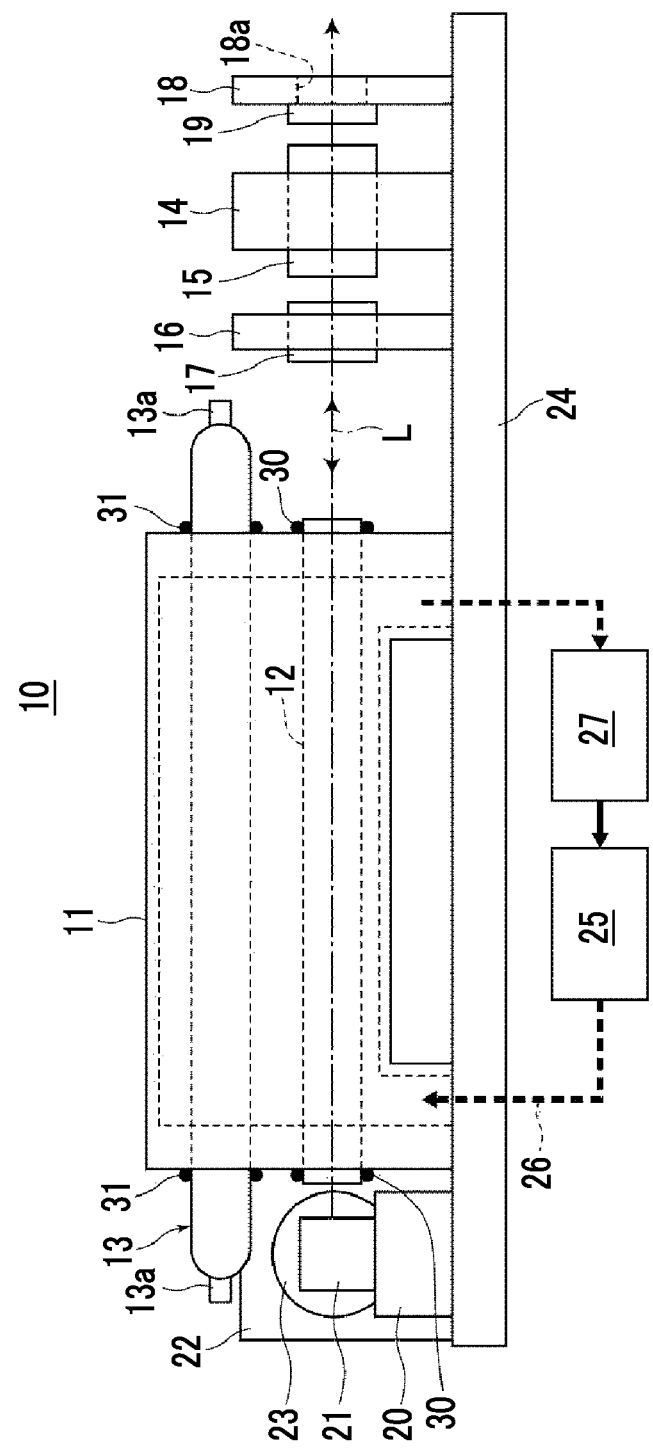
FIG. 1 is a side view showing a solid-state laser device according to a first embodiment of the invention.
Figure 2:
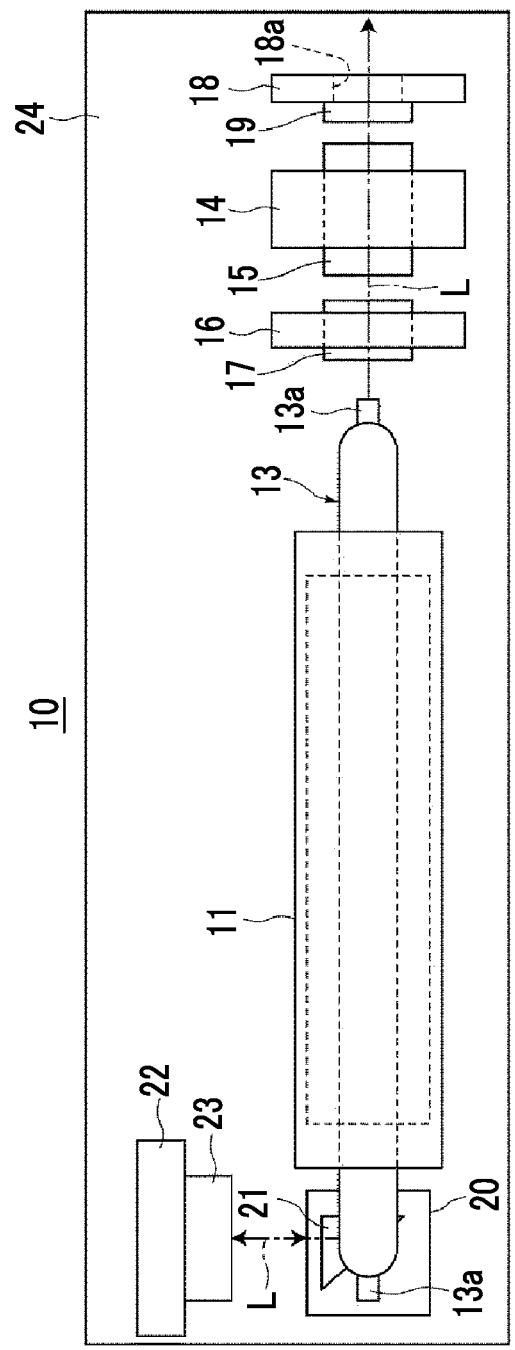
FIG. 2 is a plan view of the solid-state laser device shown in FIG. 1.

Hereinafter, an embodiment of the invention will be described in detail referring to the drawings. FIGS. 1 and 2 respectively show a side surface shape and a planar shape of a solid-state laser device 10 according to a first embodiment of the invention. In the following description, in FIGS. 1 and 2, the right side in the drawing on which a laser beam to be used is extracted is referred to as a front side or forward, and the left side in the drawing is referred to as a rear side or rearward.

The solid-state laser device 10 has a laser chamber 11 which has an appearance in a substantially rectangular parallelepiped shape, a solid-state laser medium 12, a part of which is accommodated inside the laser chamber 11, a flash lamp 13 which has a rod-shaped portion extending linearly, a part of the rod-shaped portion being provided inside the laser chamber 11, a Q switching element 15 which is attached to a holder 14, polarizer 17 which is attached to a holder 16 and is disposed between the flash lamp 13 and the Q switching element 15, a resonator mirror 19 which is attached to a holder 18, a prism 21 which serves as a reflection optical element attached to a holder 20, and a resonator mirror 23 which is attached to a holder 22. The laser chamber 11 and the holders 14, 16, 18, 20, and 22 are fixed onto a common base plate 24.

As described below in detail, the laser chamber 11 defines an internal space where a refrigerant is circulated, and for example, a refrigerant, such as pure water, is supplied into the space. That is, as shown in FIG. 1, the refrigerant is supplied into the internal space of the laser chamber 11 by a pump 25 through a piping 26, the refrigerant circulated in the internal space flows outside the laser chamber 11 through the piping 26, is cooled by a heat exchanger 27, and is then supplied into the laser chamber 11 by the pump 25 again.

The solid-state laser medium 12 is formed by processing, for example, solid-state laser crystal, such as alexandrite ($Cr:BeAl_2O_3$), neodymium YAG (Nd:YAG), or titanium sapphire ($Ti:Al_2O_3$), in a rod shape. The rod-shaped solid-state laser medium 12 is disposed parallel to the rod-shaped portion of the flash lamp 13, and both end portions thereof are held on the front wall portion and the rear wall portion of the laser chamber 11, such that most thereof is accommodated inside the laser chamber 11. The solid-state laser medium 12 is not limited to those described above, and other known solid-state laser mediums may be appropriately used.

The flash lamp 13 is an excitation light source which excites the solid-state laser medium 12, and is formed in a substantially rod shape as a whole including terminals 13a respectively formed at both ends thereof. The length of the rod-shaped portion is, for example, about 10 cm. Wires (not shown) are respectively connected to the two terminals 13a, and the flash lamp 13 is connected to a power supply for lighting through the wires. As the flash lamp 13, in more detail, for example, a xenon flash lamp or the like can be applied. The excitation light source in the solid-state laser device of the invention is not limited to the flash lamp 13, and for example, an excitation light source which has a plurality of light-emitting diodes (LEDs) disposed in parallel inside a transparent straight tube, and is formed in a rod shape as a whole, or the like may be applied.

Figure 3:
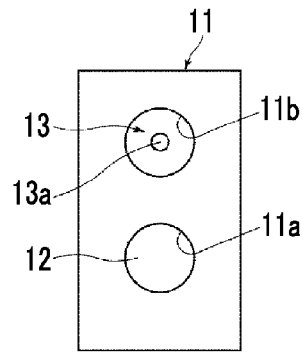
FIG. 3 is an elevational view showing a part of the solid-state laser device shown in FIG. 1.
Figure 4:
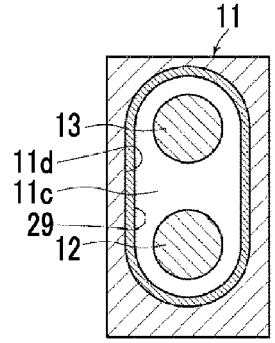
FIG. 4 is a sectional elevational view showing a part of the solid-state laser device shown in FIG. 1.

FIG. 3 shows a front shape of the laser chamber 11 which is viewed from the front side, and FIG. 4 shows a state where the laser chamber 11 is cut near a center in a forth-back direction. As shown in FIG. 3, circular through holes 11a and 11b are formed in the front wall portion of the laser chamber 11, one end portion of the solid-state laser medium 12 is inserted and held into the former through hole 11a, and one end portion of the flash lamp 13 is inserted and held into the latter through hole 11b. Though not shown, the same through holes described above are formed in the rear wall portion of the laser chamber 11, the other end portions of the solid-state laser medium 12 and the flash lamp 13 are respectively inserted and held in the through holes in the same manner as described above.

As shown in FIG. 4, a space 11c defined inside the laser chamber 11 has a substantially oval sectional shape as an example, and a part of the solid-state laser medium 12 and the flash lamp 13 is accommodated in the space so as to extend in the front-back direction. That is, the longitudinal direction of the solid-state laser medium 12 and the flash lamp 13 accommodated in the laser chamber 11 is parallel to the forth-back direction. On an inner wall surface 11d of the laser chamber 11 defining the 11c, a diffusion member 29 which diffuses and reflects light emitted from the flash lamp 13 is formed in the form of a layer.

Returning to FIG. 1, an O ring 30 is fitted to the end portion of the solid-state laser medium 12 protruding from the laser chamber 11 so as to be in contact with the outer wall surface of the laser chamber 11, and similarly, an O ring 31 is fitted to the end portion of the flash lamp 13 protruding the laser chamber 11 so as to be in contact with the outer wall surface of the laser chamber 11. Holding members (not shown) having through holes, through which the flash lamp 13 passes, are applied to the front wall portion and the rear wall portion of the laser chamber 11, and the holding members are integrated with the laser chamber 11, for example, by screwing, whereby the solid-state laser medium 12 is fixed. At this time, the O rings 30 and 31 are intensively pressed to the outer wall surface of the laser chamber 11 while being crushed by the holding members to some extent, whereby the inside and the outside of the laser chamber 11 are maintained in a high-degree watertight state.

The Q switching element 15 shown in FIGS. 1 and 2 performs a so-called Q switching operation so as to generate a high-output pulsed laser beam. The solid-state laser device of the invention is not limited to the operation to generate a pulsed laser beam, and may be configured to perform a continuous wave (CW) operation. The polarizer 17 is provided to extract only a linearly polarized component in a predetermined direction from an oscillated laser beam.

The resonator mirror 19 constitutes a laser resonator along with another resonator mirror 23. That is, the resonator mirror 23 is a high reflection mirror which has reflectance equal to or greater than, for example, 99.99%, and acts as a so-called rear mirror. The other resonator mirror 19 is a partial transmission mirror which has reflectance of, for example, about 95 to 99%, and acts as a so-called output mirror.

If the Q switching element 15 is placed in a light isolation state and the flash lamp 13 is turned on, the solid-state laser medium 12 is excited by excitation light emitted from the flash lamp 13, and an intensive inversion distribution state is formed. After this state is placed, if the Q switching element 15 is placed in a light transmission state, light L induced and emitted from the solid-state laser medium 12 is resonated between the pair of the resonator mirror 19 and the resonator mirror 23, becomes a high-output giant pulse, is transmitted through the resonator mirror 19, is transmitted through a through hole 18a of the holder 18, and is emitted outside the resonator. The flash lamp 13 and the solid-state laser medium 12 which generate heat are cooled by the refrigerant which is circulated inside the laser chamber 11.

The prism 21 is disposed at a position to face the rear end surface of the solid-state laser medium 12, and light L emitted from the rear end surface is bent in a transverse direction by the prism 21 and is incident on the resonator mirror 23 as a rear mirror. The prism 21 is provided so as not to interfere with the rod-shaped portion such that at least a part of the prism 21 and at least a part of the rod-shaped portion are at the same position in the longitudinal direction of the rod-shaped portion of the flash lamp 13, that is, in a right-left direction of FIGS. 1 and 2. Alternatively, it can be understood that, in a case of being viewed from a direction in which the solid-state laser medium 12 and the flash lamp 13 overlap each other (for example, an upward direction of FIG. 1 or a direction perpendicular to the paper surface of FIG. 2), the prism 21 is provided at a position where at least a part of the prism 21 overlaps the rod-shaped portion.

In this embodiment, the "transverse direction" is a direction perpendicular to the optical axis of the solid-state laser medium 12. However, the "transverse direction" is not limited thereto, and may be any direction as long as the direction is at an angle with respect to the longitudinal direction of the rod-shaped portion of the excitation light source. For example, in the configuration of FIG. 2, emitted light L reflected from the prism 21 may be bent in a direction of falling down to the right side in the drawing. However, in general, a direction perpendicular to the optical axis of the solid-state laser medium 12 is most preferable. The reason will be described below in detail.

The flash lamp 13 should be appropriately replaced with a new one in a case where the life has expired, or the like. For replacement, a case where the upper portion of the laser chamber 11 can be opened and the flash lamp 13 is pulled upward out of the laser chamber 11 is considered; however, if the laser chamber 11 is largely opened, it is not preferable since fine refuse or the like enters inside the laser chamber. In consideration of this point, in the solid-state laser device 10 of this embodiment employs the holding structure of the flash lamp 13 described above referring to FIG. 3, and the flash lamp 13 is pulled rearward out of the laser chamber 11.

However, in this case, if the prism 21 is not disposed, and if the resonator mirror 23 is at a position to face the rear end surface of the solid-state laser medium 12 (it is assumed that the distance from the rear end surface is identical in this embodiment), even though the flash lamp 13 is pulled rearward out of the laser chamber 11, the flash lamp 13 interferes with the holder 22 for the resonator mirror 23, and thus, cannot be pulled out. In order to avoid the interference, if the resonator mirror 23 is disposed at a large distance from the rear end surface of the solid-state laser medium 12, the solid-state laser device 10 is increased in size. Furthermore, in order to avoid the interference, if the flash lamp 13 and the solid-state laser medium 12 are disposed at a large distance from each other, excitation efficiency is lowered.

In contrast, in this embodiment, the prism 21 which bends the optical path is provided, whereby the resonator mirror 23 and the holder 22 are provided at positions (see FIG. 2) not to interfere with the rod-shaped portion of the flash lamp 13 being pulled out. In other words, the resonator mirror 23 and the holder 22 are disposed at positions separated from each other in a path along which the flash lamp 13 is pulled out. Accordingly, for pulling the flash lamp 13 out, since the flash lamp 13 does not come into contact with the resonator mirror 23 and the holder 22, the flash lamp 13 can be completely pulled out of the laser chamber 11. Furthermore, according to this configuration, it is possible to prevent an increase in the size of the solid-state laser device 10 in the above-described manner. In addition, since it is not necessary to dispose the flash lamp 13 and the solid-state laser medium 12 at a large distance from each other, it is possible to prevent excitation efficiency from being lowered.

The reflective surface of the resonator mirror 23 should have a large area to some extent, and the holder 22 also has a large size to some extent since an optical axis adjustment mechanism of the resonator mirror 23 is provided, or the like. For this reason, it is difficult to provide the resonator mirror 23 at a position to face the rear end surface of the solid-state laser medium 12 such that the resonator mirror 23 and the holder 22 are reduced in size so as not to interfere with the flash lamp 13.

On the other hand, as the prism 21 which simply bends the optical path, a comparatively small prism can be applied. Accordingly, even though at least a part of the prism 21 and at least a part of the rod-shaped portion are disposed at the same position in the longitudinal direction of the rod-shaped portion of the flash lamp 13 as described above, the position on a plane perpendicular to the longitudinal direction is shifted, whereby the prism 21 can be disposed in a state of being separated from the rod-shaped portion. Specifically, in a three-dimensional space represented by the X axis, the Y axis, and the Z axis, in a case where the longitudinal direction of the rod-shaped portion of the flash lamp 13 is referred to as the X-axis direction, the prism 21 and the flash lamp 13 are partially identical in the x coordinate and are different in at least one of the Y coordinate and the Z coordinate. The prism 21 is disposed in the above-described manner, whereby it is possible to avoid interference of the flash lamp 13 being pulled out and the prism 21. In this way, if the prism 21 is disposed at a position sufficiently close to the rear end surface of the solid-state laser medium 12, the distance between the rear end surface and the resonator mirror 23 can be sufficiently reduced. With this, the size of the device can be sufficiently reduced, and in addition, the resonator length is maintained short and a pulsed laser beam with a sufficiently short pulse width is obtained.

Here, the reason that the pulsed laser beam with a short pulse width is preferable will be described. The magnitude of the photoacoustic wave generated by the irradiation of the pulsed laser beam depends on not only the total energy of the pulsed laser beam but also the time waveform of the pulsed laser beam. For example, when the time waveform of the pulsed laser beam changes gently, the photoacoustic wave to be generated is not so large, and as the time waveform of the pulsed laser beam changes more steeply, the magnitude of the photoacoustic wave to be generated becomes larger. That is, the time variation of light intensity is correlated with the magnitude of the photoacoustic wave. Accordingly, in order to secure large signal intensity of the photoacoustic wave to be generated and the detection signal, it is preferable that a pulsed laser beam with a large time variation of light intensity and a short pulse width (time width) is used.

In order to maintain the distance between the solid-state laser medium 12 and the resonator mirror 23 short, as described above, it is preferable that light L emitted from the rear end surface of the solid-state laser medium 12 is bent in a direction perpendicular to the optical axis of the solid-state laser medium 12.

As described above, in a case where the flash lamp 13 and the solid-state laser medium 12 are arranged on the upper side and the lower side, if the flash lamp 13 is disposed on the upper side, an operation to pull the flash lamp 13 out is further facilitated.

Figure 19:
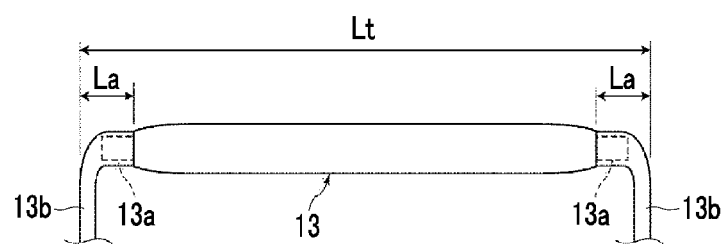
FIG. 19 is a schematic view illustrating a rod-shaped portion of an excitation light source.
Figure 20:
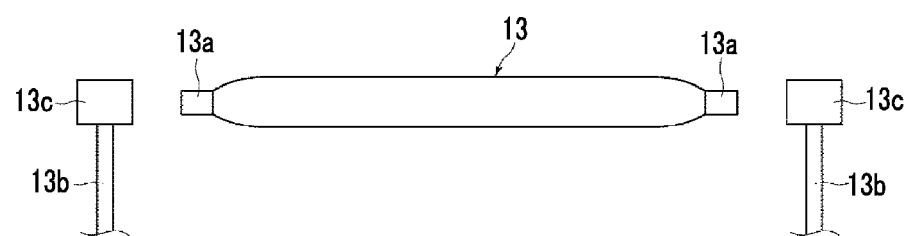
FIG. 20 is a schematic view illustrating the rod-shaped portion of the excitation light source.
Figure 21:
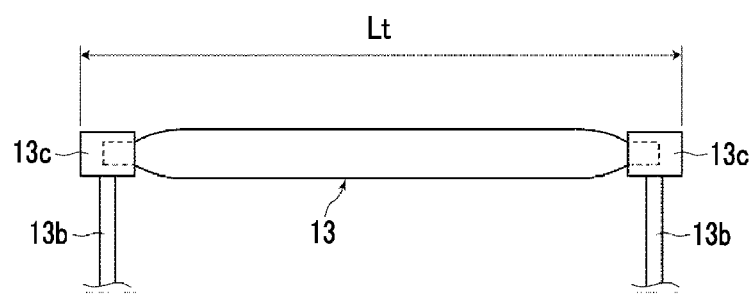
FIG. 21 is a schematic view illustrating the rod-shaped portion of the excitation light source.

As described above, in this embodiment, although the rod-shaped portion of the flash lamp 13 includes not only the light-emitting portion but also the terminals 13a of both ends, a "rod-shaped portion" of an excitation light source in the invention is not limited to such a form, and indicates a portion which is formed in a rod shape as a whole. That is, for example, as shown in FIG. 19, in a configuration in which lead wires 13b are connected to the terminals 13a of the flash lamp 13, in both end portions indicated by La in the drawing, if not only the terminals 13a but also the end portions of the unbent lead wires 13b are in a rod shape along with the light-emitting portion, the range of Lt including both end portions La is referred to as the "rod-shaped portion". In addition, as shown in FIG. 20, in a configuration in which connectors 13c are mounted on the lead wires 13b, and the lead wires 13b are connected to the terminals 13a through the connectors 13c, as shown in FIG. 21 showing a state after connection, the range of Lt including the connectors 13c of both ends is referred to as the "rod-shaped portion".

Figure 5:
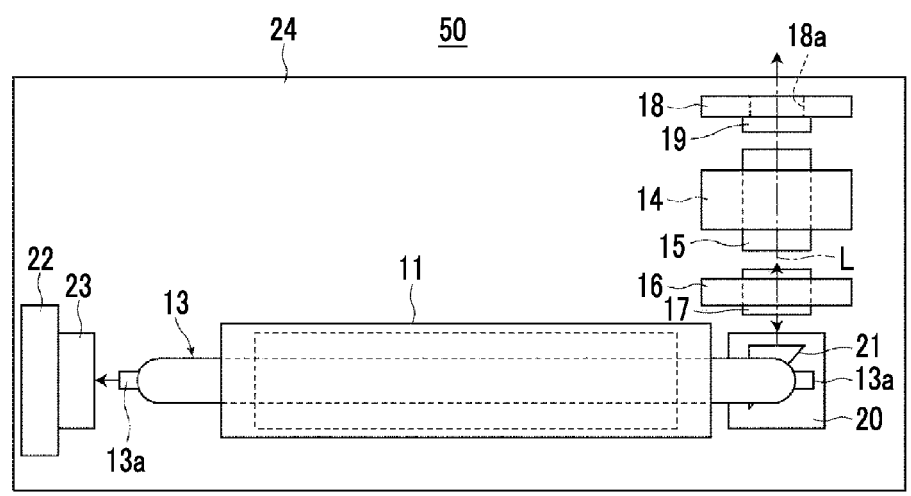
FIG. 5 is a plan view showing a solid-state laser device according to a second embodiment of the invention.

Next, a second embodiment of the invention will be described referring to FIG. 5. In FIG. 5, the same components as the components in FIGS. 1 to 4 are represented by the same reference numerals, and description thereof will not be repeated unless particularly necessary (the same applies hereinafter).

A solid-state laser device 50 of the second embodiment is configured such that the flash lamp 13 is pulled out of the laser chamber 11 forward, that is, rightward in the drawing. That is, in this device, the resonator mirror 23 as a rear mirror is disposed in a state of facing the rear end surface of the solid-state laser medium 12 (see FIG. 1) (not shown) held in the laser chamber 11, and the prism 21 is disposed in a state of facing the front end surface of the solid-state laser medium 12. The prism 21 bends light L emitted from the front end surface of the solid-state laser medium 12 in a direction perpendicular to the optical axis of the solid-state laser medium 12.

In the solid-state laser device 50 of this embodiment having the above configuration, the flash lamp 13 which is pulled out rightward in the drawing does not interfere with the polarizer 17, the holder 16, or the like, and the flash lamp 13 can be extracted from the laser chamber 11.

Figure 6:
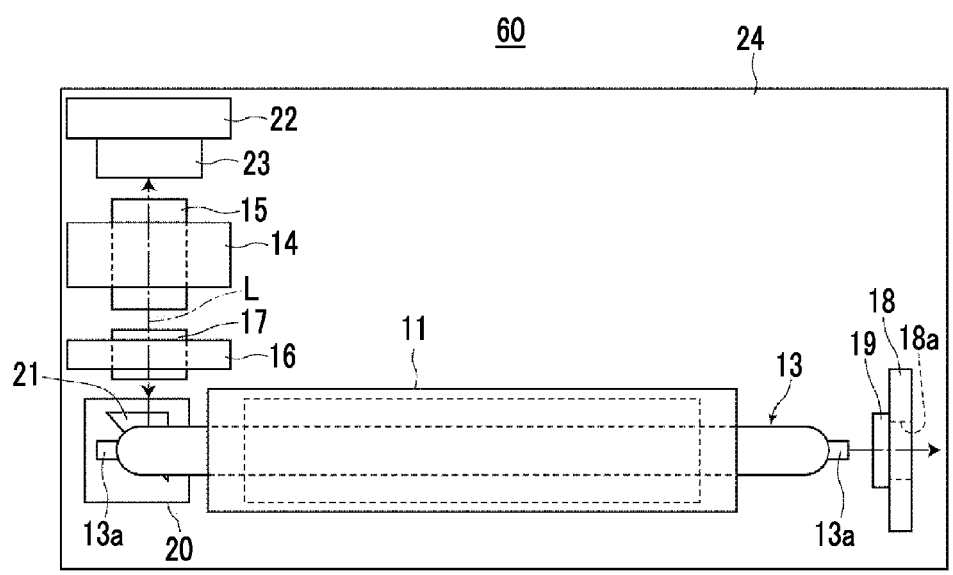
FIG. 6 is a plan view showing a solid-state laser device according to a third embodiment of the invention.

Next, a third embodiment of the invention will be described referring to FIG. 6. A solid-state laser device 60 of the third embodiment is configured such that the flash lamp 13 is pulled out of the laser chamber 11 rearward, that is, leftward in the drawing. That is, in this device, the prism 21 is provided similarly to that in the solid-state laser device 10 shown in FIGS. 1 and 2.

The solid-state laser device 60 of this embodiment is basically different from the solid-state laser device 10 shown in FIGS. 1 and 2 only in that the Q switching element 15 and the polarizer 17 are disposed between the resonator mirror 23 as a rear mirror and the prism 21. In the solid-state laser device 60 of this embodiment having the above configuration, the flash lamp 13 which is pulled out leftward in the drawing does not interfere with the polarizer 17, the holder 16, or the like, and the flash lamp 13 can be completely extracted from the laser chamber 11.

Figure 7:
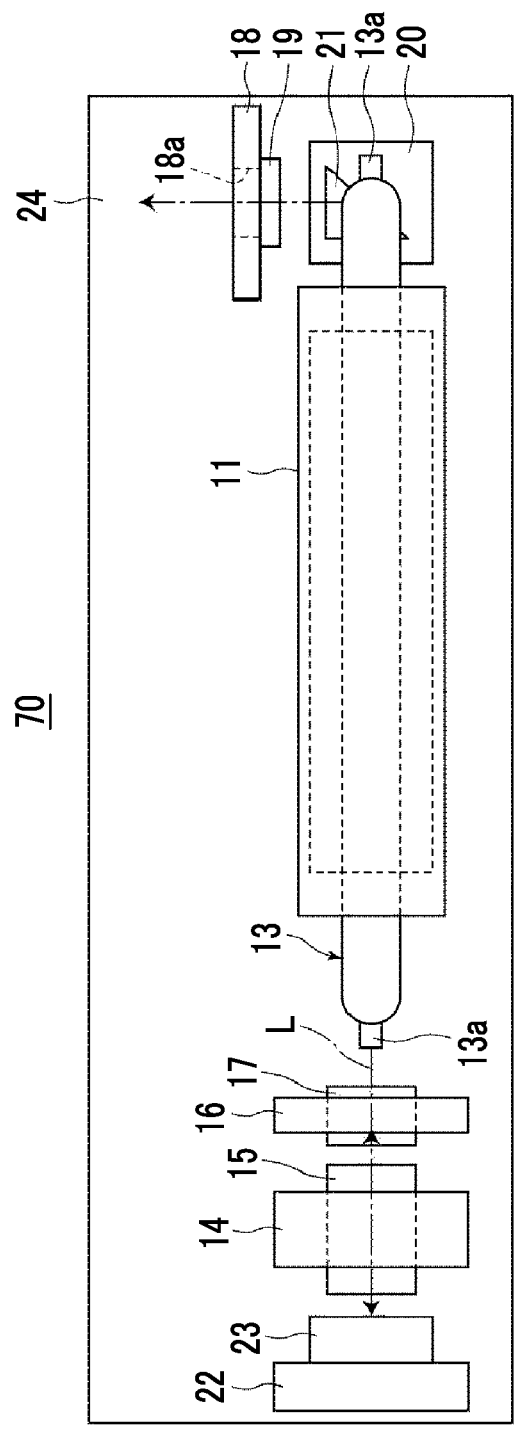
FIG. 7 is a plan view showing a solid-state laser device according to a fourth embodiment of the invention.

Next, a fourth embodiment of the invention will be described referring to FIG. 7. A solid-state laser device 70 of the fourth embodiment is configured such that the flash lamp 13 is pulled out of the laser chamber 11 forward, that is, rightward in the drawing. That is, in this device, the prism 21 is provided similarly to the prism 21 in the solid-state laser device 50 shown in FIG. 5.

The solid-state laser device 70 of this embodiment is basically different from the solid-state laser device 50 shown in FIG. 5 only in that the Q switching element 15 and the polarizer 17 are disposed between the resonator mirror 23 as a rear mirror and the solid-state laser medium (not shown). In the solid-state laser device 70 of this embodiment having the above configuration, the flash lamp 13 which is pulled out rightward in the drawing does not interfere with the resonator mirror 19 as an output mirror and the holder 18, and the flash lamp 13 can be completely extracted from the laser chamber 11.

A reflection optical element is not limited to the prism 21, and a mirror or the like may be applied. In a case where linearly polarized light L is emitted from the solid-state laser medium 12, in particular, the polarizer 17 may not be disposed. In addition, the optical path bent by the prism 21 may be bent in an arbitrary direction by an additional element.

Figure 8:
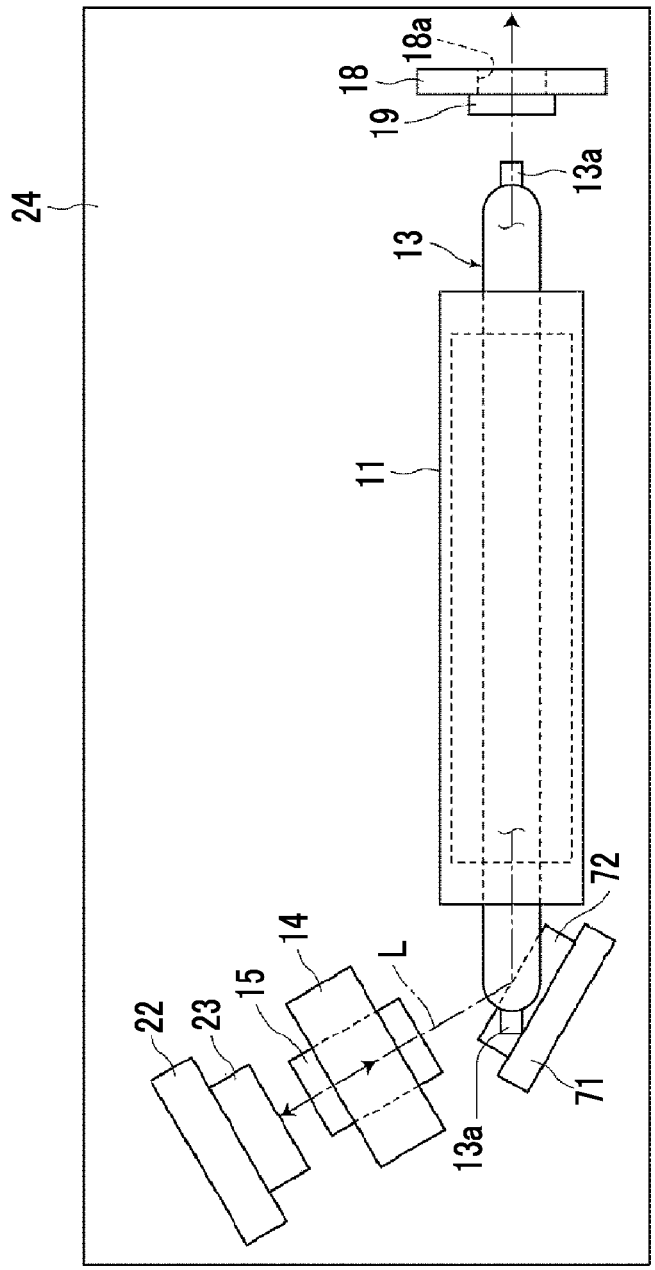
FIG. 8 is a plan view showing a solid-state laser device according to a fifth embodiment of the invention.

Next, a fifth embodiment of the invention will be described referring to FIG. 8. A solid-state laser device 80 of the fifth embodiment is configured such that the flash lamp 13 is pulled out of the laser chamber 11 rearward, that is, leftward in the drawing. That is, in this device, as the optical element which bends light L in the transverse direction, a Brewster polarizer 72 attached to a holder 71 is used. The Brewster polarizer 72 acts to extract only an S-polarized component from an oscillated laser beam and to reflect the S-polarized component. Then, the Brewster polarizer 72 and the holder 71 are provided so as not to interfere with the rod-shaped portion such that at least a part of the Brewster polarizer 72 and the holder 71 and at least a part of the rod-shaped portion are at the same position in the longitudinal direction of the rod-shaped portion of the flash lamp 13, that is, in the right-left direction of FIG. 8. The Brewster polarizer 72 and the holder 71 are disposed at positions not to interfere with the flash lamp 13 to be pulled out.

In the solid-state laser device 80 of this embodiment having the above configuration, the flash lamp 13 which is pulled out leftward in the drawing does not interfere with the Q switching element 15, the holder 14, or the like, and the flash lamp 13 can be completely extracted from the laser chamber 11.

Figure 9:
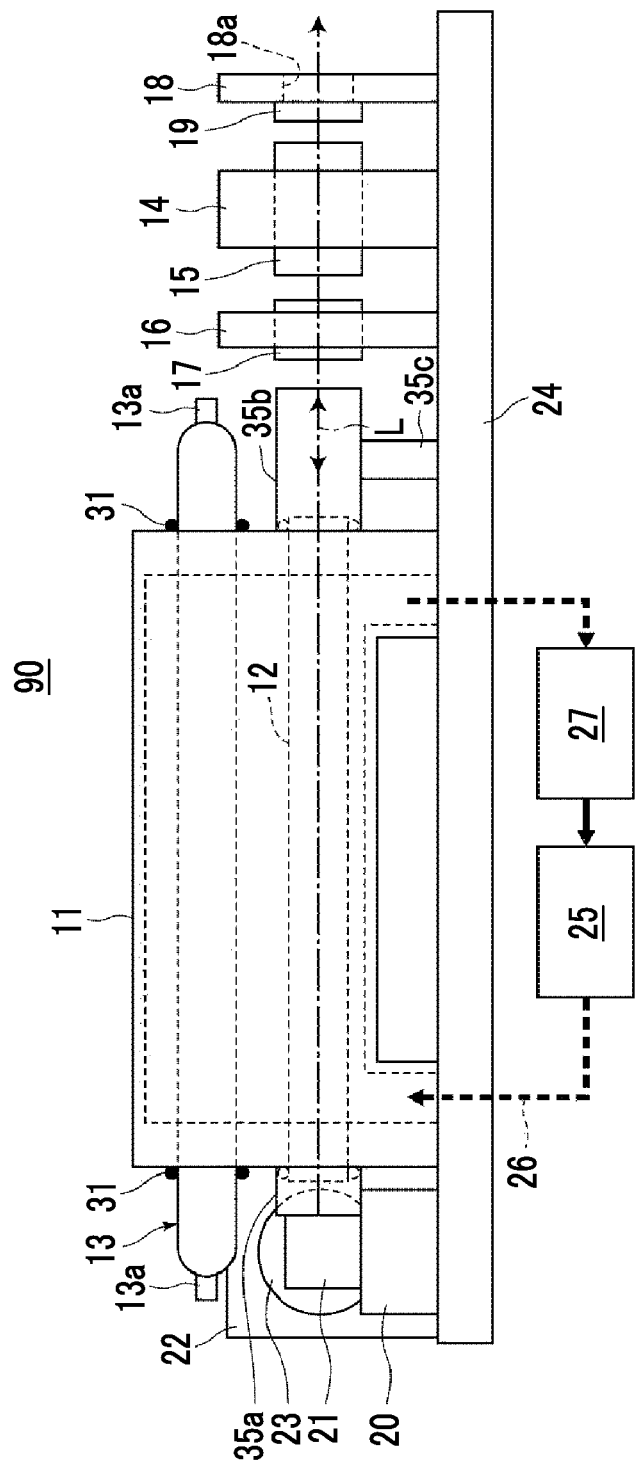
FIG. 9 is a side view showing a solid-state laser device according to a sixth embodiment of the invention.
Figure 10:
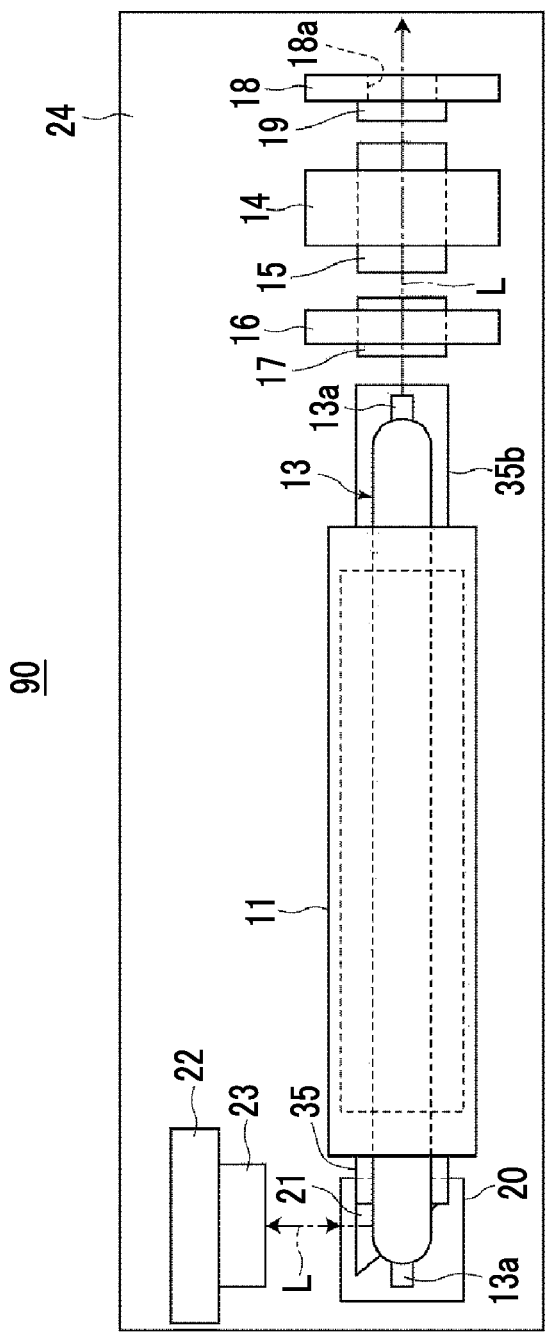
FIG. 10 is a plan view showing the solid-state laser device shown in FIG. 9.

Next, a sixth embodiment of the invention will be described referring to FIGS. 9 and 10. A solid-state laser device 90 of the sixth embodiment has a configuration in which a cylinder member 35a surrounding an optical path between the solid-state laser medium 12 and the prism 21 and a cylinder member 35b surrounding an optical path between the solid-state laser medium 12 and the polarizer 17 are added to the solid-state laser device 10 of the first embodiment. That is, the cylinder members 35a and 35b are cylindrical members which encapsulate the optical paths between the solid-state laser medium 12 and the prism 21 and between the solid-state laser medium 12 and the polarizer 17. The cylinder member 35a is held by the holder 20, and the cylinder member 35b is held by a holder 35c. If gas (air) warmed around the flash lamp 13 flows into the optical paths, fluctuation (so-called shimmer) in refractive index is generated, and stability of laser beam intensity is lowered. In particular, in the invention, since the distance between the flash lamp 13 and the solid-state laser medium 12 is close, the influence of the shimmer is not small. Accordingly, in this embodiment, the cylinder members 35a and 35b are disposed to prevent warmed gas from flowing into the optical paths, whereby stability of laser beam intensity is secured.

The shape of the cylinder members 35a and 35b is not particularly limited, and is, for example, a hollow columnar member, a quadrangular prismatic member, or other polygonal prismatic members. The width (the length in a direction perpendicular to the center axis or the optical path) of the inner periphery of the cylinder members 35a and 35b is not particularly limited, and may be equal to or longer than the width of the solid-state laser medium 12. However, the total size of the cylinder members 35a and 35b is of a size not to interfere with the flash lamp 13 for pulling the flash lamp 13 out rearward. The length of the cylinder member 35a along the center axis or the optical axis is not particularly limited, and is preferably a length enough to cover the entire optical path between the solid-state laser medium 12 and the prism 21. The length of the cylinder member 35b along the center axis or the optical axis is not particularly limited, and can be appropriately set in consideration of the degree of influence of the shimmer, and the entire optical path between the solid-state laser medium 12 and the polarizer 17 may not necessarily be covered. This is because the interval between the solid-state laser medium 12 and the polarizer 17 is longer than the interval between the solid-state laser medium 12 and the prism 21, and thus only a region where the influence of the shimmer is large may be covered. It is preferable that the cylinder members 35a and 35b respectively cover the end portion of the solid-state laser medium 12 simultaneously with the optical path between the solid-state laser medium 12 and the prism 21 or simultaneously with the optical path between the solid-state laser medium 12 and the polarizer 17. The material for the cylinder members 35a and 35b is not particularly limited, and is, for example, a metal material, a glass material, or a plastic material. In the above description, although a case where both of the cylinder members 35a and 35b are provided has been described, either cylinder member may be provided.

In the solid-state laser device 90 of this embodiment having the above configuration, as in the first embodiment, it is possible to prevent interference with other members when the flash lamp 13 is pulled out, and to suppress lowering of stability of light intensity when the flash lamp 13 and the solid-state laser medium 12 are brought close to each other.

Figure 11:
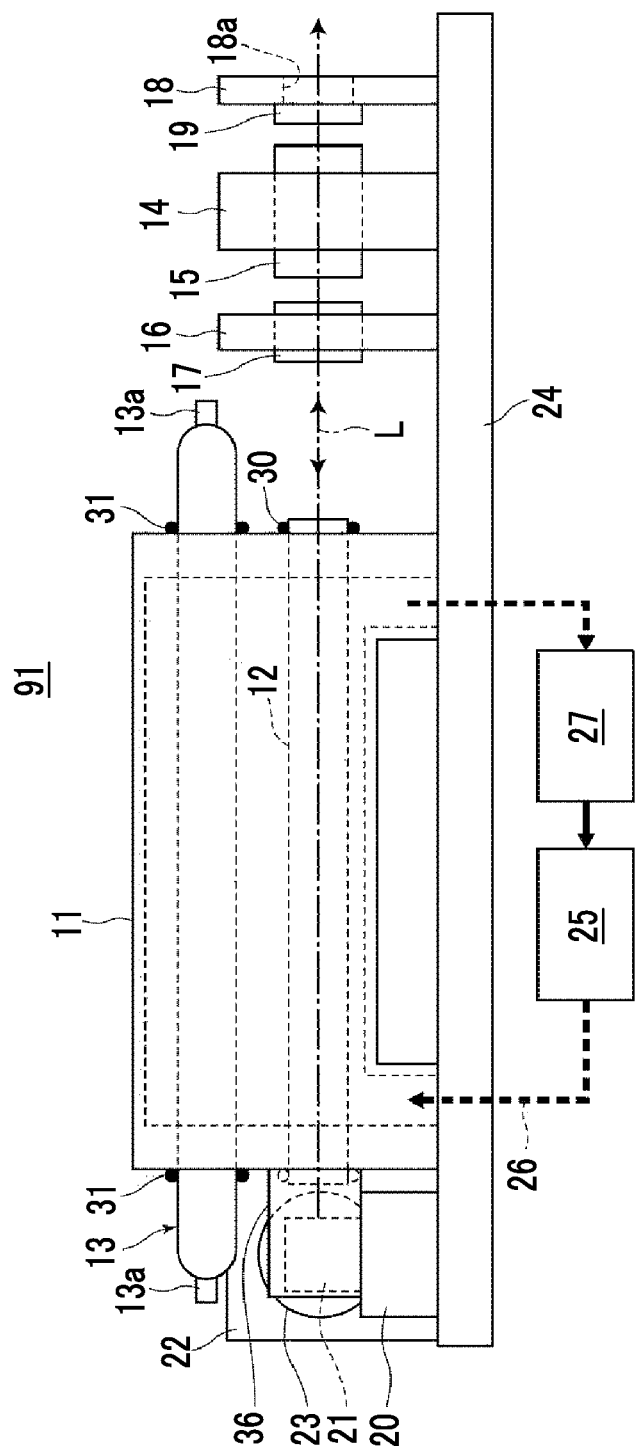
FIG. 11 is a side view showing a solid-state laser device according to a seventh embodiment of the invention.
Figure 12:
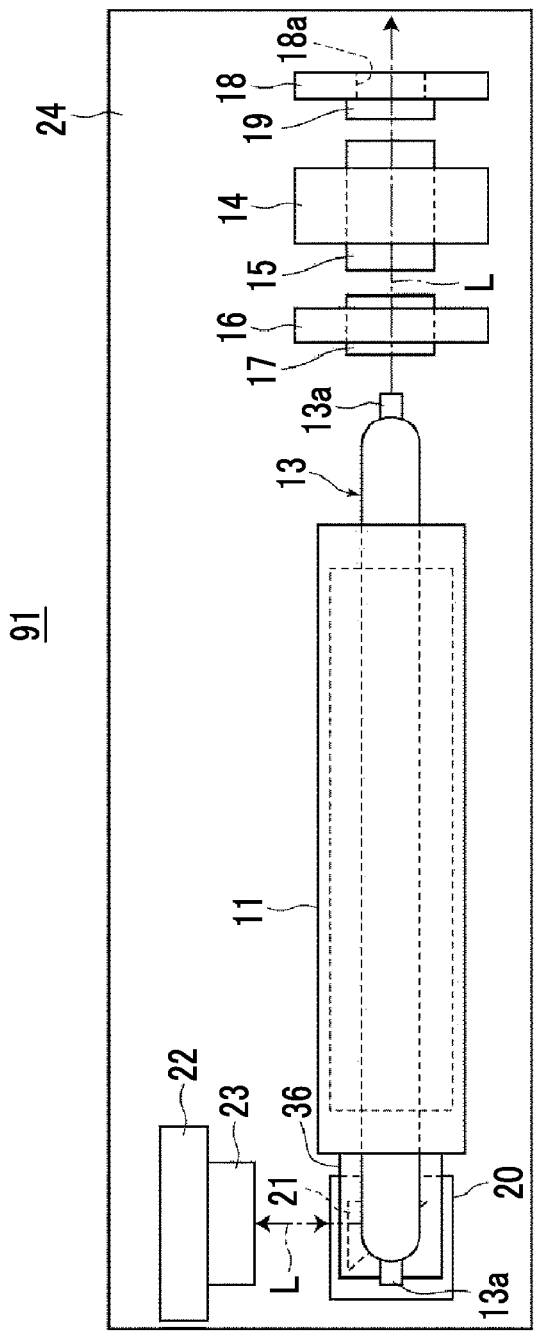
FIG. 12 is a plan view showing the solid-state laser device shown in FIG. 11.

Next, a seventh embodiment of the invention will be described referring to FIGS. 11 and 12. A solid-state laser device 91 of the seventh embodiment has a cylinder member similarly to the solid-state laser device 90 of the sixth embodiment, and is different from the device of the sixth embodiment in that a cylinder member 36 of the solid-state laser device 91 covers the prism 21 simultaneously with the optical path between the solid-state laser medium 12 and the prism 21. In this way, the prism 21 is covered with the cylinder member 36 simultaneously, whereby it is possible to more reliably prevent warmed gas from flowing into the optical path between the solid-state laser medium 12 and the prism 21 from the gap between the cylinder member 36 and the prism 21. In order to secure the optical path of the laser beam L bent by the prism 21, an opening or a light window filled with a light transmissive member is formed in the side surface portion of the cylinder member 36. Though not specified in FIGS. 11 and 12, as in the sixth embodiment, a cylinder member may be provided between the solid-state laser medium 12 and the polarizer 17. In the solid-state laser device 91 of this embodiment having the above configuration, the same effects as in the sixth embodiment are obtained.

In the sixth and seventh embodiments, although the cylinder member is used in order to prevent warmed air from flowing into the optical paths, in order to attain the above-described object, the inflow of gas between the flash lamp 13 and each optical path may be blocked, and the invention is not necessarily limited to the use of the cylindrical member. For example, as such a member, similarly, a plate-shaped member (for example, a U-shaped, L-shaped, or semicircular plate, or a simple flat plate) formed of a metal material, a glass material, or a plastic material may be used.

Figure 13:
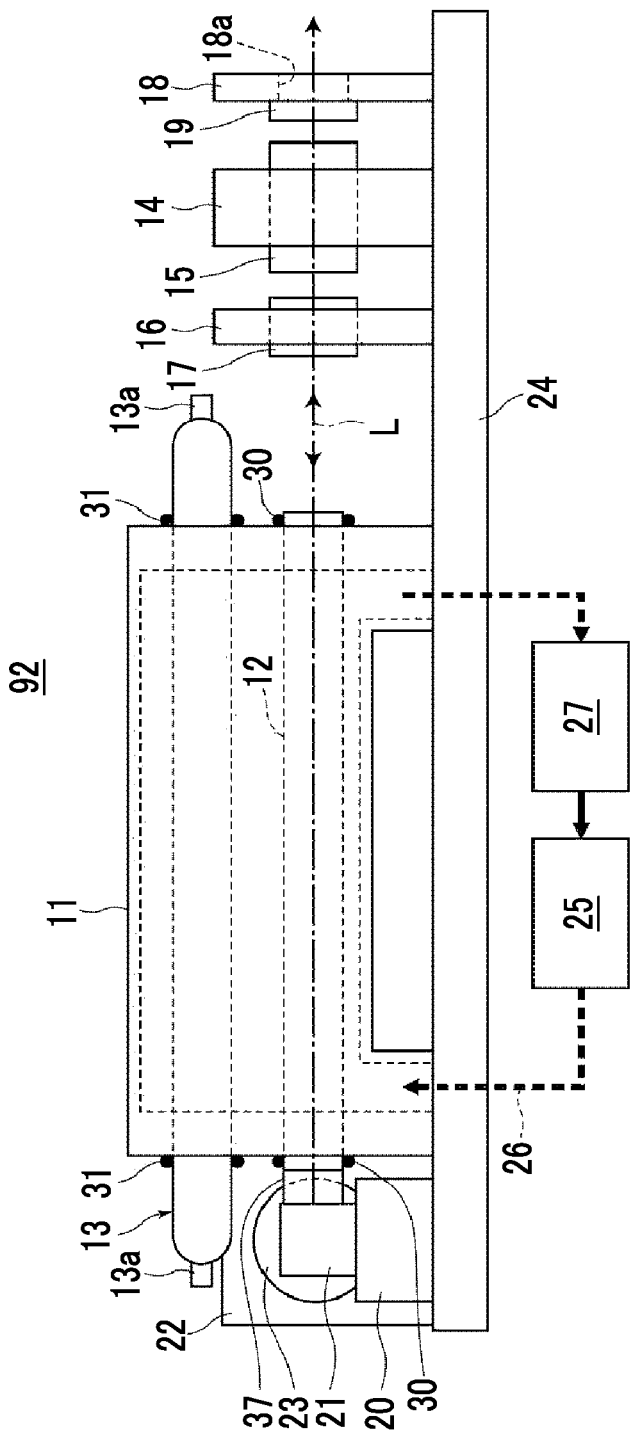
FIG. 13 is a side view showing a solid-state laser device according to an eighth embodiment of the invention.

Next, an eighth embodiment of the invention will be described referring to FIG. 13. A solid-state laser device 92 of the eighth embodiment has a configuration in which a light guide member 37 optically connecting the solid-state laser medium 12 and the prism 21 is added to the solid-state laser device 10 of the first embodiment. That is, in this embodiment, a laser beam L reciprocates between the solid-state laser medium 12 and the prism 21 through the light guide member without going into a gas space. In this way, the solid-state laser medium 12 and the prism 21 are connected using the light guide member 37, whereby it is possible to prevent warmed gas from flowing into the optical path between the solid-state laser medium 12 and the prism 21.

It is preferable that the light guide member 37 has an antireflection film (AR coat) which is formed on both end surfaces. Alternatively, it is preferable that the light guide member 37 is disposed to be bonded to the solid-state laser medium 12 or the prism 21 through optical contact without using an adhesive. The width or the diameter of the light guide member 37 may be greater than the solid-state laser medium 12. However, the width or diameter of the light guide member 37 is of a size not to interfere with the flash lamp 13 for pulling the flash lamp 13 out rearward. The material for the light guide member 37 is, for example, a light transmissive material, such as quartz glass or acryl. Though not specified in FIG. 13, a light guide member may be provided in the whole or a part between the solid-state laser medium 12 and the polarizer 17. In a case where the optical element which bends the optical path is a mirror or a Brewster polarizer, it is possible to bring the end surface of the light guide member as close to the reflective surface as possible. In the solid-state laser device 92 of this embodiment having the above configuration, the same effects as in the sixth embodiment are obtained.

Figure 14:
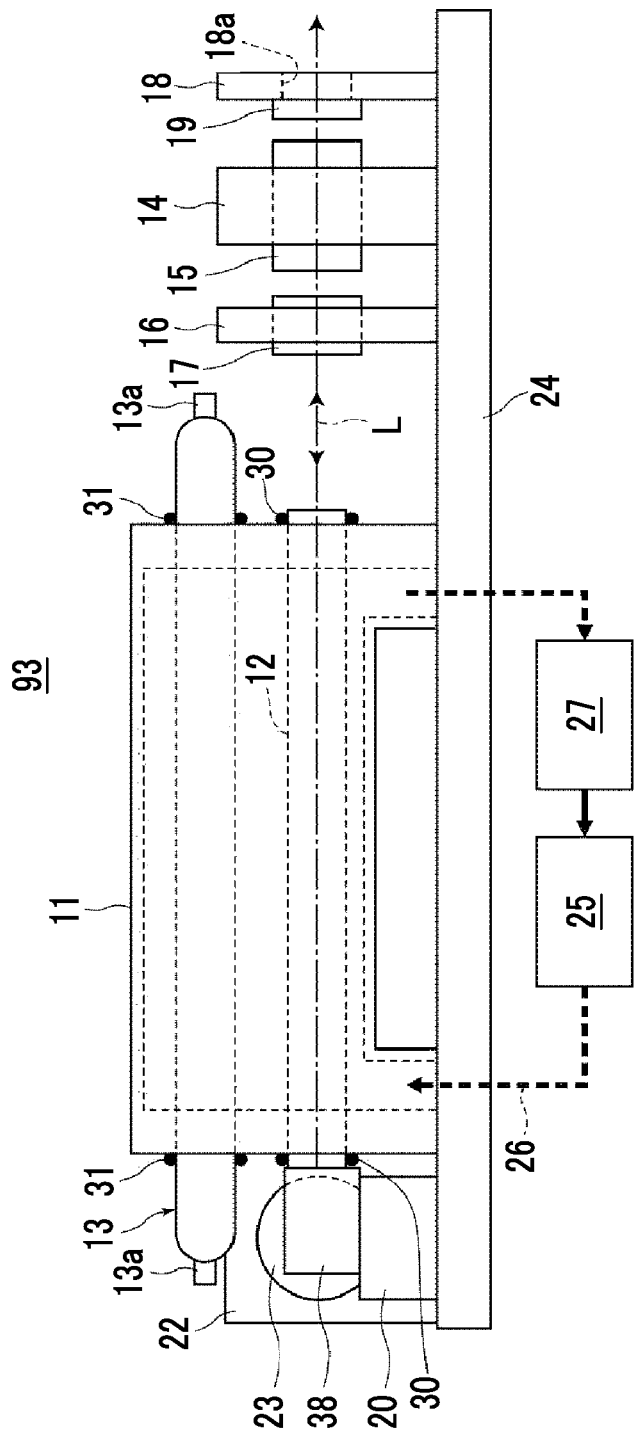
FIG. 14 is a side view showing a solid-state laser device according to a ninth embodiment of the invention.
Figure 15:
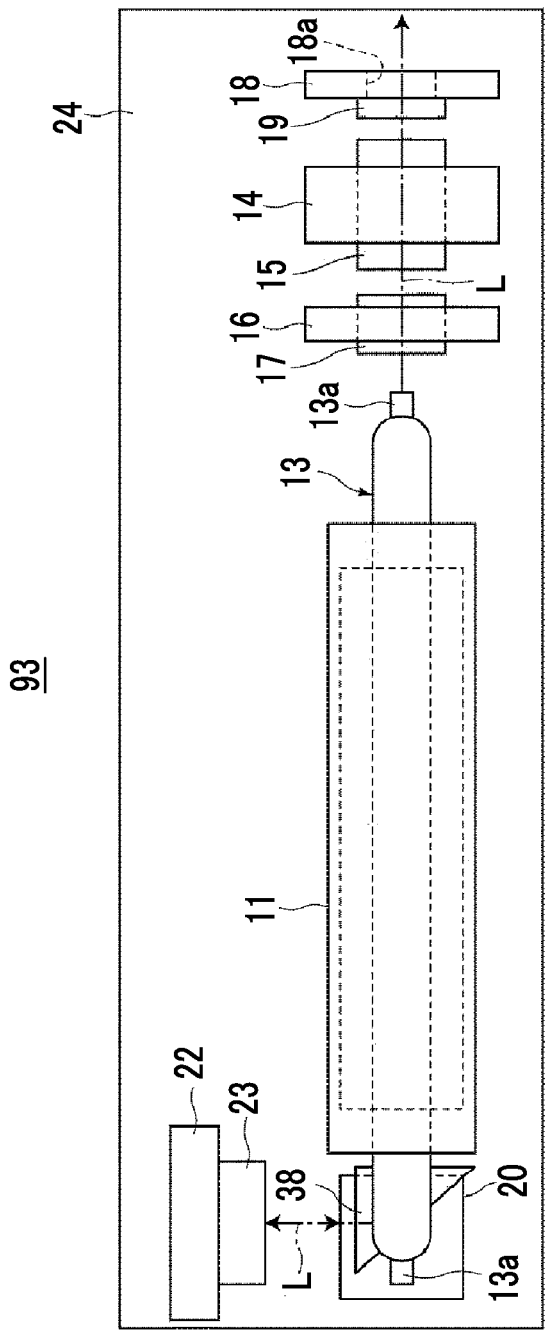
FIG. 15 is a plan view showing the solid-state laser device shown in FIG. 14.

Next, a ninth embodiment of the invention will be described referring to FIGS. 14 and 15. A solid-state laser device 93 of the ninth embodiment has a configuration in which, in the solid-state laser device 10 of the first embodiment, instead of the prism 21, a prism 38 which is optically connectable directly to the solid-state laser medium 12 is used. That is, in this embodiment, a laser beam L is moved directly between the solid-state laser medium 12 and the prism 38 without going into a gas space. In this way, the solid-state laser medium 12 and the prism 38 are connected directly to each other, whereby the gas space where which is likely to be affected by the shimmer can be excluded between the solid-state laser medium 12 and the prism 38.

It is preferable that the prism 38 has an antireflection film formed on an incidence/emission surface facing the solid-state laser medium 12. Alternatively, it is preferable that the prism 38 is disposed to be bonded to the solid-state laser medium 12 through optical contact. The size and shape of the prism 38 are not particularly limited, and have a size and a shape not to interfere with the flash lamp 13 for pulling the flash lamp 13 out rearward. The material for the prism 38 is, for example, a light transmissive material, such as quartz glass or acryl, similarly to the prism 21. In the solid-state laser device 93 of this embodiment having the above configuration, the same effects as in the sixth embodiment are obtained.

In the sixth to ninth embodiments, although a method of securing stability of laser beam intensity has been described, different embodiments among the embodiments may be combined in each end portion of the solid-state laser medium 12. That is, the sixth or seventh embodiment (cylinder member) may be applied to the rear end portion of the solid-state laser medium 12 and the eighth embodiment (light guide member) may be applied to the front end portion. The ninth embodiment (direct connection to the prism) may be applied to the rear end portion of the solid-state laser medium 12 and the sixth embodiment (cylinder member) or the eighth embodiment (light guide member) may be applied to the front end portion.

In the respective embodiments described above, although the invention is applied to a solid-state laser device in which the Q switching element 15 and the polarizer 17 or the Brewster polarizer 72 are provided inside a resonator, the invention can be similarly applied to a solid-state laser device in which other elements, for example, various wavelength plates, wavelength selection elements, or the like are provided inside a resonator.

Figure 16:
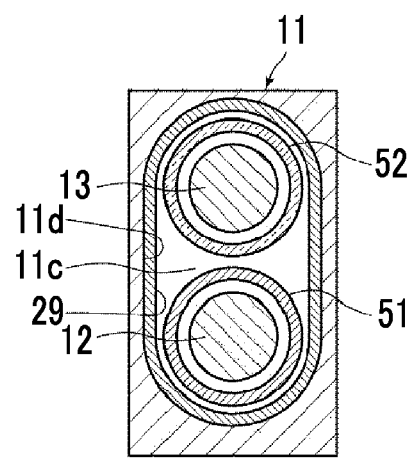
FIG. 16 is a sectional elevational view showing an example of a laser chamber.

Next, another example of the laser chamber 11 which can be applied to the solid-state laser device of the invention will be described. A laser chamber 11 shown in FIG. 16 is basically different from the laser chamber 11 shown in FIG. 4 in that tubes 51 and 52 are provided in an internal space 11c. The tube 51 accommodates the solid-state laser medium 12 and extends in the same direction as the solid-state laser medium 12. The tube 52 accommodates the flash lamp 13 and extends in the same direction as the flash lamp 13. Then, a refrigerant is supplied into the tubes 51 and 52, and the solid-state laser medium 12 and the flash lamp 13 are cooled by the refrigerant which is circulated in the tubes 51 and 52.

The tubes 51 and 52 are formed of a light transmissive material. Accordingly, excitation light emitted from the flash lamp 13 is transmitted through the tubes 51 and 52 and the solid-state laser medium 12 is irradiated with excitation light, whereby the solid-state laser medium 12 is excited by excitation light.

Figure 17:
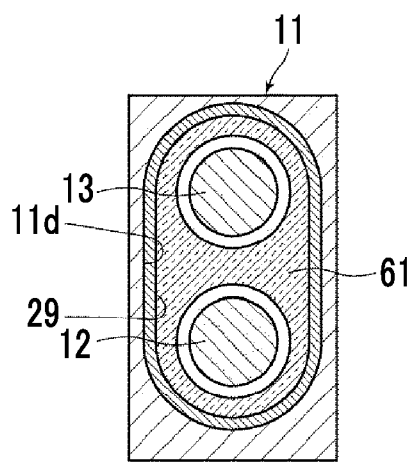
FIG. 17 is a sectional elevational view showing another example of a laser chamber.

Next, a laser chamber 11 shown in FIG. 17 is basically different from the laser chamber 11 shown in FIG. 4 in that a glass material 61 is filled inside the laser chamber 11. The glass material 61 has a through hole which extends in the same direction as the solid-state laser medium 12 and accommodates the solid-state laser medium 12, and a through hole which extends in the same direction as the flash lamp 13 and accommodates the flash lamp 13. The refrigerant is supplied into the two through holes, and the solid-state laser medium 12 and the flash lamp 13 are cooled by the refrigerant which is circulated in the through holes.

Excitation light emitted from the flash lamp 13 is transmitted through the glass material 61 and the solid-state laser medium 12 is irradiated with excitation light, whereby the solid-state laser medium 12 is excited by excitation light.

In the solid-state laser device of the invention, an element, such as the prism 21, which bends the optical path may be disposed in front of or at the rear of the laser chamber, and the excitation light source having the rod-shaped portion may be configured to be pulled out toward both of the front side and the rear side of the laser chamber.

Figure 18:
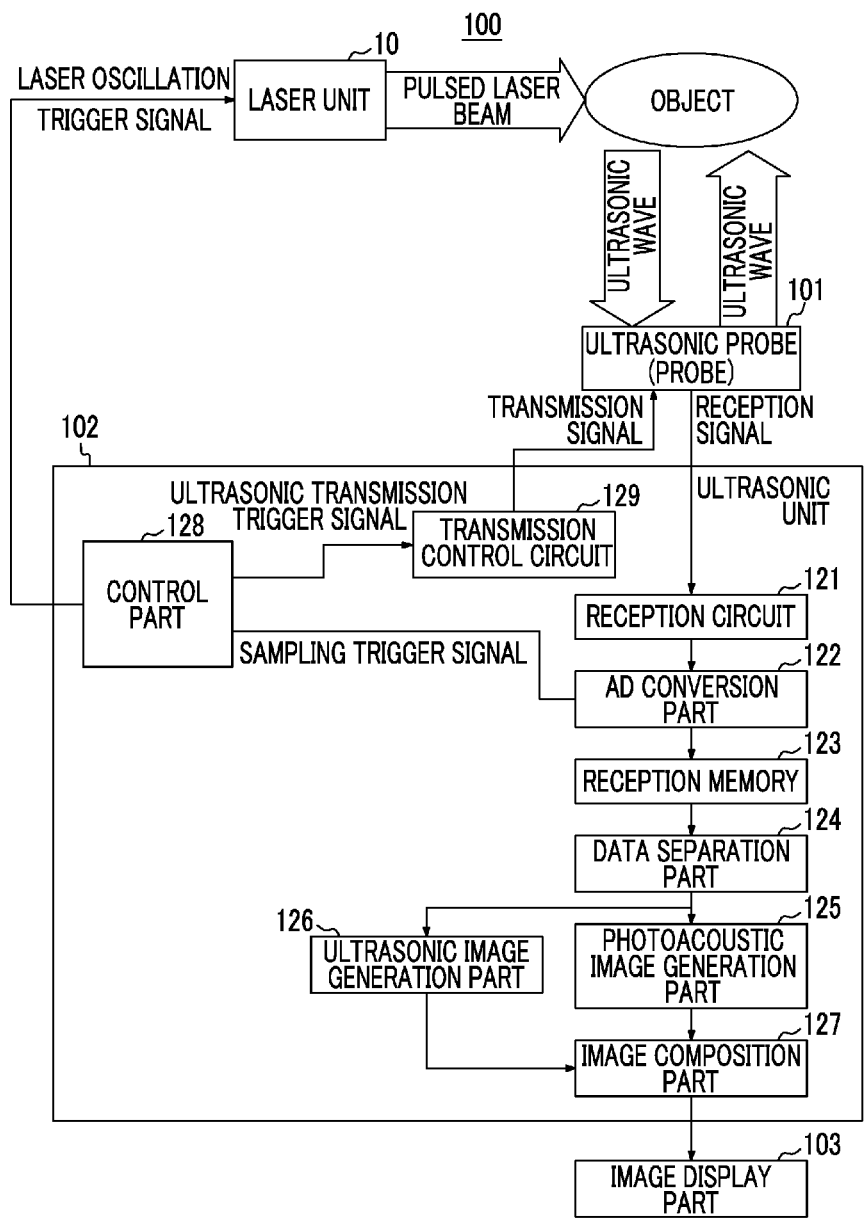
FIG. 18 is a schematic configuration diagram showing an embodiment of a photoacoustic measurement device according to the invention.

Next, a photoacoustic measurement device including the solid-state laser device of the invention will be described. FIG. 18 shows the schematic configuration of a photoacoustic measurement device including the solid-state laser device 10 shown in FIGS. 1 and 2 as an example. In FIG. 18, the solid-state laser device 10 is considered to be one unit constituting the photoacoustic measurement device and is thus described as a "laser unit", and hereinafter, the solid-state laser device 10 is referred to as the laser unit.

A photoacoustic measurement device 100 includes an ultrasound probe (probe) 101, an ultrasound unit 102, and a laser unit 10. In this embodiment, although an ultrasonic wave is used as an acoustic wave, the invention is not limited to the ultrasonic wave, and an acoustic wave having an audio frequency may be used as long as an appropriate frequency has to be selected according to an inspection target, the measurement conditions, or the like.

A laser beam emitted from the laser unit 10 is guided to the probe 101, for example, using light guide means, such as an optical fiber, and is irradiated from the probe 101 toward a subject. The irradiation position of the laser beam is not particularly limited, and the irradiation of the laser beam may be performed from a place other than the probe 101.

Inside the subject, an optical absorber absorbs energy of the irradiated laser beam, and thus, an ultrasonic wave (photoacoustic wave) is generated. The probe 101 is acoustic wave detection part, and has, for example, a plurality of ultrasonic vibrators arranged in a one-dimensional manner. The probe 101 detects an acoustic wave (photoacoustic wave) from the inside of the subject by a plurality of ultrasonic vibrators arranged in a one-dimensional manner. The probe 101 transmits an acoustic wave (ultrasonic wave) to the subject and receives a reflected acoustic wave (reflected ultrasonic wave) of the transmitted ultrasonic wave reflected from the inside of the subject.

The ultrasound unit 102 is signal processing part, and has a reception circuit 121, an AD conversion part 122, a reception memory 123, a data separation part 124, a photoacoustic image generation part 125, an ultrasound image generation part 126, an image composition part 127, a control part 128, and a transmission control circuit 129.

The reception circuit 121 receives a detection signal of the photoacoustic wave detected by the probe 101, and receives a detection signal of the reflected ultrasonic wave detected by the probe 101. The AD conversion part 122 converts the detection signals of the photoacoustic wave and the reflected ultrasonic wave received by the reception circuit 121 to digital signals. The AD conversion part 122 samples the detection signals of the photoacoustic wave and the reflected ultrasonic wave in a predetermined sampling period based on, for example, a sampling clock signal having a predetermined period. The AD conversion part 122 stores the sampled detection signals (sampling data) of the photoacoustic wave and the reflected ultrasonic wave in the reception memory 123.

The data separation part 124 separates sampling data of the detection signal of the photoacoustic wave stored in the reception memory 123 from sampling data of the detection signal of the reflected ultrasonic wave. The data separation part 124 inputs sampling data of the detection signal of the photoacoustic wave to the photoacoustic image generation part 125, and inputs the separated sampling data of the reflected ultrasonic wave to the ultrasound image generation part (reflected acoustic image generation part) 126.

The photoacoustic image generation part 125 generates a photoacoustic image based on the detection signal of the photoacoustic wave detected by the probe 101. The generation of the photoacoustic image includes, for example, image reconstruction, such as phase matching addition, detection, logarithmic conversion, and the like. The ultrasound image generation part 126 generates an ultrasound image (reflected acoustic image) based on the detection signal of the reflected ultrasonic wave detected by the probe 101. The generation of the ultrasound image includes image reconstruction, such as phase matching addition, detection, logarithmic conversion, and the like.

The image composition part 127 composes the photoacoustic image and the ultrasound image. For example, the image composition part 127 performs image composition by overlapping the photoacoustic image and the ultrasound image. A composite image is displayed on image display part 103, such as a display. Image composition may not be performed, and the photoacoustic image and the ultrasound image may be displayed in parallel on the image display part 103, or the photoacoustic image and the ultrasound image may be switched and displayed.

The control part 128 controls the respective units in the ultrasound unit 102. For example, the control part 128 sends a trigger signal to the solid-state laser device. If the trigger signal is received, control part (not shown) in the laser unit 10 turns on the flash lamp 13 (see FIG. 1), and then, switches the Q switching element 15 to a light transmission state to emit a pulsed laser beam. The control part 128 sends a sampling trigger signal to the AD conversion part 122 according to the irradiation of the laser beam, and controls a sampling start timing of the photoacoustic wave.

The control part 128 sends an ultrasonic transmission trigger signal to instruct the transmission control circuit 129 to transmit the ultrasonic wave at the time of the generation of the ultrasound image. If the ultrasonic transmission trigger signal is received, the transmission control circuit 129 allows the ultrasonic wave to be transmitted from the probe 101. The control part 128 sends the sampling trigger signal to the AD conversion part 122 according to the ultrasonic transmission timing, and starts the sampling of the reflected ultrasonic wave.

The photoacoustic measurement device 100 of this embodiment includes the solid-state laser device 10 of the invention as a light source, and thus, can be formed in a sufficiently small size.

In the above description, although a case where the probe 101 detects both the photoacoustic wave and the reflected ultrasonic wave in the photoacoustic measurement device 100 has been described, the probe for use in generating the ultrasound image and the probe for use in generating the photoacoustic image may not necessarily be the same. That is, the photoacoustic wave and the reflected ultrasonic wave may be respectively detected by different probes. Furthermore, in the foregoing embodiments, although an example where the solid-state laser device constitutes a part of the photoacoustic measurement device has been described, the solid-state laser device of the invention can be of course used for a device different from the photoacoustic measurement device.

Although the invention has been described based on the preferred embodiment, the solid-state laser device and the photoacoustic measurement device of the invention are not limited to the foregoing embodiments, and various alterations may be carried out from the configurations of the foregoing embodiments and may fall within the scope of the invention.

EXPLANATION OF REFERENCES

10, 50, 60, 70, 80: solid-state laser device
11: laser chamber
11*a*, 11*b*: through hole of laser chamber
11*c*: internal space of laser chamber
11*d*: inner wall surface of laser chamber
12: solid-state laser medium
13: flash lamp
14, 16, 18, 20, 22, 71: holder
15: Q switching element
17: polarizer
19, 23: resonator mirror
21, 38: prism (optical element)
24: base plate 25: pump
26: piping
27: heat exchanger
29: diffusion member
35a, 35b, 36: cylinder member
37: light guide member
51, 52: tube
61: glass material
72: Brewster polarizer (optical element)
100: photoacoustic measurement device

What is claimed is:

1. A solid-state laser device comprising:
a laser chamber which has an internal space;
a solid-state laser medium, at least a part of which is accommodated in the laser chamber;
an excitation light source which has a rod-shaped portion extending linearly, a part of the rod-shaped portion being provided inside the laser chamber as a portion emitting excitation light exciting the solid-state laser medium, and both end portions being provided outside the laser chamber; and
a pair of resonator mirrors which resonate light emitted from both end portions of the excited solid-state laser medium,
wherein the rod-shaped portion of the excitation light source is provided to be moved in a longitudinal direction of the rod-shaped portion and capable of being pulled out of the laser chamber,
an optical element which bends light emitted from one end surface of the solid-state laser medium in a transverse direction is provided to face the one end surface of the solid-state laser medium,
the optical element is provided at a position separated from the rod-shaped portion such that at least a part of the optical element and at least a part of the rod-shaped portion are at the same position in the longitudinal direction of the rod-shaped portion,
one of the pair of resonator mirrors is disposed at a position where light bent by the optical element is incident, and
optical components between the optical element and the one resonator mirror are provided at positions separated from a path along which the rod-shaped portion of the excitation light source is pulled out.

2. The solid-state laser device according to claim 1, wherein the solid-state laser device has a configuration for generating a pulsed laser beam.

3. The solid-state laser device according to claim 1, wherein the optical element is disposed on an optical path between a resonator mirror as a rear mirror and the solid-state laser medium.

4. The solid-state laser device according to claim 2, wherein the optical element is disposed on an optical path between a resonator mirror as a rear mirror and the solid-state laser medium.

5. The solid-state laser device according to claim 1, wherein the optical element is disposed on an optical path between a resonator mirror as an output mirror and the solid-state laser medium.

6. The solid-state laser device according to claim 2, wherein the optical element is disposed on an optical path between a resonator mirror as an output mirror and the solid-state laser medium.

7. The solid-state laser device according to claim 1, wherein the optical element is a prism.

8. The solid-state laser device according to claim 1, wherein the optical element is a mirror.

9. The solid-state laser device according to claim 1, wherein the optical element is a Brewster polarizer.

10. The solid-state laser device according to claim 1, wherein the excitation light source is a flash lamp.

11. The solid-state laser device according to claim 1, wherein the rod-shaped portion of the excitation light source is held in through holes formed in two wall portions of the laser chamber separated from each other in the longitudinal direction of the rod-shaped portion.

12. The solid-state laser device according to claim 1, wherein the solid-state laser medium is formed in a rod shape, and the solid-state laser medium is disposed parallel to the rod-shaped portion of the excitation light source.

13. The solid-state laser device according to claim 1, wherein a refrigerant is supplied into the internal space of the laser chamber.

14. The solid-state laser device according to claim 1, wherein a diffusion member which diffuses and reflects excitation light emitted from the excitation light source is formed on an inner wall surface of the laser chamber.

15. The solid-state laser device according to claim 1, wherein a cylinder member which encapsulates an optical path between the solid-state laser medium and the optical element is provided.

16. The solid-state laser device according to claim 15, wherein the cylinder member further encapsulates the optical element.

17. The solid-state laser device according to claim 1, wherein a plate-shaped member is disposed between an optical path between the solid-state laser medium and the optical element and the excitation light source.

18. The solid-state laser device according to claim 1, wherein a light guide member is disposed on an optical path between the solid-state laser medium and the optical element.

19. The solid-state laser device according to claim 7, wherein the solid-state laser medium and the prism are optically connected directly to each other.

20. A photoacoustic measurement device comprising:
the solid-state laser device according to claim 1;
a photoacoustic wave detection part which detects a photoacoustic wave generated inside an object by irradiating the object with laser light emitted from the solid-state laser device; and
a signal processing part which performs a signal process based on the detected photoacoustic wave.

* * * * *